US012605052B2

(12) United States Patent
Schulz et al.

(10) Patent No.: US 12,605,052 B2
(45) Date of Patent: Apr. 21, 2026

(54) ALBARRAN AND PULL WIRE CARRIER FOR AN ALBARRAN

(71) Applicant: OLYMPUS WINTER & IBE GMBH, Hamburg (DE)

(72) Inventors: Kevin Schulz, Wilstedt (DE); Irina Schmuck, Heide (DE); Bastian Schroeder, Hamburg (DE); Andreas Ruehs, Ahrensburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 506 days.

(21) Appl. No.: 18/078,409

(22) Filed: Dec. 9, 2022

(65) Prior Publication Data

US 2024/0188809 A1    Jun. 13, 2024

Related U.S. Application Data

(60) Provisional application No. 63/296,320, filed on Jan. 4, 2022.

(51) Int. Cl.
  A61B 1/005 (2006.01)
  A61B 1/00 (2006.01)
(52) U.S. Cl.
  CPC ........ A61B 1/0057 (2013.01); A61B 1/00098 (2013.01)
(58) Field of Classification Search
  CPC .......................... A61B 1/00098; A61B 1/0057
  See application file for complete search history.

(56) References Cited

U.S. PATENT DOCUMENTS

| | | | | |
|---|---|---|---|---|
| 5,372,587 | A | * 12/1994 | Hammerslag | ..... A61M 25/0144 |
| | | | | 604/95.04 |
| 5,569,157 | A | 10/1996 | Nakazawa et al. | |
| 2018/0125567 | A1 | 5/2018 | Ciccone et al. | |
| 2020/0323591 | A1 | 10/2020 | Ransome | |
| 2021/0244264 | A1 | 8/2021 | Schulz | |
| 2023/0233067 | A1 * | 7/2023 | Lund | .................... A61B 1/0052 |
| | | | | 600/104 |

FOREIGN PATENT DOCUMENTS

| | | |
|---|---|---|
| EP | 3861918 A1 | 8/2021 |
| WO | 2021/193693 A1 | 9/2021 |
| WO | 2021/249601 A1 | 12/2021 |

* cited by examiner

*Primary Examiner* — Erin McGrath
(74) *Attorney, Agent, or Firm* — Oliff PLC

(57) ABSTRACT

An Albarran and a pull wire carrier are particularly efficiently usable as well as producible and reconditionable. The pull wire carrier for an Albarran includes a through-bore for a tubular shaft. This pull wire carrier can be mounted in a drive body of the Albarran, pull wires for the actuation of a lever of the Albarran being braceable on the pull wire carrier. This pull wire carrier is characterized by a receptacle into which a cover element can be placed, the cover element being releasably connectable to the pull wire carrier. The at least one pull wire is fixable between the pull wire carrier and the cover element.

12 Claims, 4 Drawing Sheets

35   11

36

37

35   11

34

34

ALBARRAN AND PULL WIRE CARRIER FOR AN ALBARRAN

Figures 1, 2:
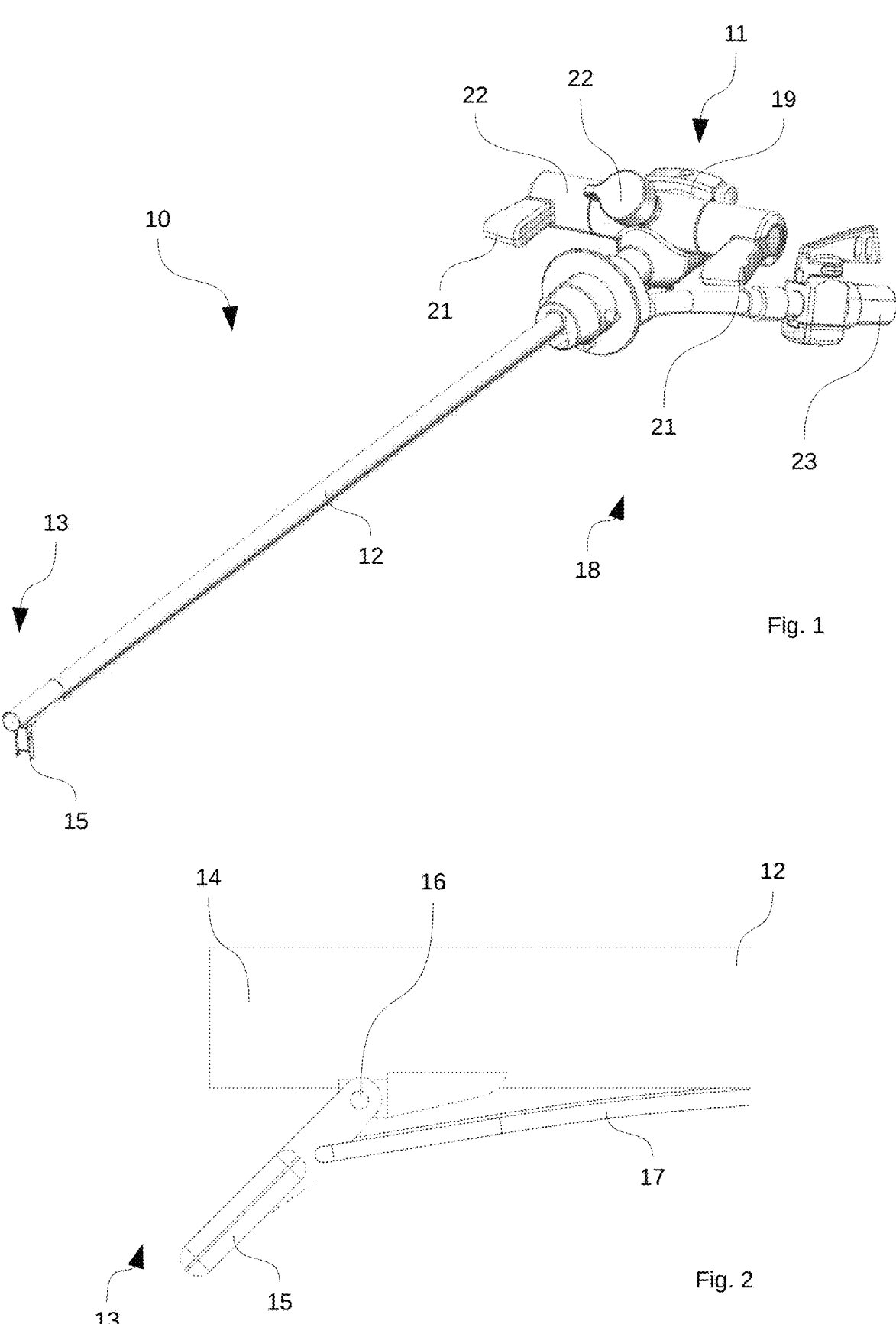

The invention relates to a pull wire carrier according to the preamble of claim 1. The invention furthermore relates to an Albarran as claimed in claim 12.

Albarrans are used to assist in operations or treatments with surgical instruments, for example endoscopes, resectoscopes, cystoscopes or the like. An Albarran may, for example, be used to move flexible forceps in the interior of a patient in a purposeful and controlled way. For this purpose the Albarran, in the same way as for example an endoscope, comprises a shaft in the form of a rod or tube, which is to be guided with a distal end into the body of the patient. At a proximal end of the Albarran, outside the patient, the shaft is connected to a main body. Via this main body, further instruments or tools, for example an optical unit, wires or the like can be guided via various openings, or ports, through the shaft into the patient.

At the distal end of the shaft, the Albarran comprises a lever, the so-called Albarran lever. This lever is configured to be movable and can be actuated, or pivoted, by means of a toggle on the main body. For this purpose, the lever is mechanically coupled to the toggle along the shaft. This mechanical coupling may involve either a rod or a pull wire. In general, the lever is connected to the toggle by means of two pull wires. It is conceivable for the two pull wires to be used equally for pivoting the lever to and fro, or for different movements of the lever to be achievable by means of the two pull wires via the toggle.

For reliable operation of the Albarran lever, the pull wires need to be braced inside the main body, in a drive body therein with a pull wire carrier. This means that the pull wires are screwed with mechanical tensioning during known assembly methods. For this purpose, the pull wires are each fixed by a grub screw. So that the grub screws can brace the pull wire, the wire needs to be made deformable by means of annealing. This step is particularly difficult since the wire already laid in the instrument needs to be subjected to sufficiently high thermal energy in the main body and then to be braced with the grub screw. Since this bracing has to be done from the side, i.e. transversely with respect to a longitudinal axis of the shaft, this assembly step must take place before the installation of the toggle or of a toggle axle. The grub screws are screwed through the free openings for the toggles in the drive body. Overall, this assembly proves very difficult, complicated and therefore prone to error. If the main body of the Albarran does not allow such lateral access to the pull wire, this type of bracing cannot be carried out. Furthermore, the material of the pull wire carrier must be configured in such a way that it withstands both the input of heat and the mechanical stress due to the grub screws.

For reconditioning of the Albarran, or of the main body, it is essential that all components, in particular internal components, can be flushed, disinfected and sterilized and are arranged with respect to one another in such a way that they do not form any flushing shadows or dead volumes that are difficult to clean. These requirements are not satisfied merely by the materials of the known systems. Furthermore, the spacings between moving components or between contact surfaces, for example the tubular shaft and the pull wire carrier, are not cleanable. Without being able to achieve the necessary thoroughness in the reconditioning, surgical instruments such as the Albarran described here, and its components, cannot be reused. However, providing or using complex instruments of this type as single-use instruments is too expensive.

In order to satisfy the aforementioned requirements, it is particularly essential not to lose sight of the nature of the materials used and the dimensioning of the individual components. Especially in the case of mechanical components via which forces are to be exerted, it is necessary to ensure that the mechanical stability is sufficient to withstand even sizeable stresses. Likewise, it is necessary to bear in mind that components suffer from a defect, particularly when used incorrectly. The consequences entailed by such a defect for the treatment, as well as for the patient, must be taken into account in the selection of the materials, or in the dimensioning of all the components. Likewise, measures with which it is possible to respond to possible defects of individual components are necessary.

The object of the invention is to provide an Albarran and a pull wire carrier, which can be used as well as produced and reconditioned particularly efficiently.

A solution to this object is described by the features of claim 1. Provision is accordingly made that a pull wire carrier for an Albarran comprises a through-bore for a tubular shaft. This pull wire carrier can be mounted in a drive body of the Albarran, pull wires for the actuation of a lever of the Albarran being braceable on the pull wire carrier. This pull wire carrier is characterized by a receptacle, into which a cover element can be inserted, the cover element being releasably connectable to the pull wire carrier. The at least one pull wire can be fixed between the pull wire carrier and the cover element. This fixing of the at least one pull wire by the cover element can be carried out from the proximal side of the pull wire carrier, and is therefore not restricted by the design of the drive body. The pull wire can be fixed in a simple, secure and therefore reliable way between the cover element and the pull wire carrier, Because of this purely mechanical fixing, the hitherto required heating, or annealing, of the wire becomes superfluous.

Preferably, the invention furthermore provides that the cover element can be clamped, pressed, adhesively bonded and/or screwed in the receptacle of the pull wire carrier. By the aforementioned types of fixing, it is possible to ensure that the at least one pull wire is fastened on the pull wire carrier under the required mechanical tension. Both by clamping, pressing and by screwing, the at least one pull wire can be fastened on the pull wire carrier under defined conditions. This is advantageous in particular for reproducible and therefore reliable assembly of the Albarran.

In particular, the invention furthermore provides that the cover element is placed in the receptacle with a predetermined pressure, preferably that the cover element can be screwed by an end side with a defined torque against a receptacle side of the receptacle of the pull wire carrier. The invention may, in particular, provide that the proximal end of the at least one pull wire can be laid against or bent around the receptacle side of the receptacle of the pull wire carrier and can be clamped between the receptacle side of the receptacle of the pull wire carrier and the end side of the cover element, so that a friction clutch of the pull wire is formed between the receptacle side and the end side. The effect of this friction clutch of the pull wire is that, in the event of incorrect use or a mechanical defect, the pull wire disengages from the pull wire carrier, or from the connection between the pull wire carrier and the cover element. This, for example, may prevent the lever or the axle of the lever from breaking or a pull wire from tearing. In particular, unpredictable complications may occur during the treatment in particular because of mechanical damage to the lever and/or to the axle. By the friction clutch described above, such mechanical damage can be counteracted in a defined way. By the use of a predetermined torque for the fastening of the wire ends in the pull wire carrier, this friction clutch may be adjusted with a high accuracy.

The invention may furthermore provide that one or two bores for the receptacle of one or two pull wires are arranged in the pull wire carrier, the bores extending from a distal side of the pull wire carrier to the receptacle side of the receptacle of the pull wire. The pull wires may be guided through these bores in a defined and secure way to the proximal end of the pull wire carrier, where they are fixed. The distal openings of these bores may be slightly enlarged in order to reduce the sliding resistance and to facilitate the threading of the wires into the bores. It is conceivable for these bores to have a non-zero angle in relation to a longitudinal axis of the Albarran, in order to optimize the feeding of the wires to the receptacle side of the pull wire carrier. Likewise, however, provision is made for the bores to be aligned parallel with the longitudinal axis of the Albarran.

A further advantageous exemplary embodiment of the invention may provide that the through-bore, which is in particular circular, in the pull wire carrier comprises one, two or more recesses for receiving a tube on an inner wall. These recesses preferably extend parallel to a longitudinal axis of the Albarran, over the entire length of the through-bore. These recesses behave in an advantageous manner when flushing the Albarran or the main body. When flushing around and through the pull wire carrier, the flushing liquid can flow through this recess along the inner wall of the through-bore and the lateral surface of the tube. By this flushing around with a flushing liquid, in particular a heated flushing liquid, a high degree of cleaning or sterilization may be achieved, so that reconditioning of the instrument becomes possible.

It may be provided according to the invention that the one, two or more recesses occupy from 10% to 40%, preferably 20%, of the area of the inner wall of the through-bore of the pull wire carrier. The greater the sum of the areas of the recess is, the greater the achievable cleaning performance is. However, an increasing area of the recess also reduces the quality of the guiding of the shaft inside the pull wire carrier. The aforementioned area ratio has therefore proven particularly advantageous for the use of the present instrument.

In addition, the invention may provide that a diameter of the through-bore is greater than a diameter of a tube, or shaft, that can be received in the through-bore, an annular gap being formed between the inner wall of the through-bore and the tube. Here as well, the annular gap is to be kept as small as possible in order not to detrimentally influence the required guiding of the tube inside the pull wire carrier. Likewise, the pull wire carrier or the through-bore can be flushed more thoroughly when the annular gap is configured to be larger.

Furthermore, it may be provided by the invention that a cross section of the pull wire carrier is configured in the manner of a wedge or trapezoid, the cross section tapering toward an upper end of the pull wire carrier. By this shape of the upper section of the pull wire carrier, a flushing flow which impinges on the pull wire carrier from above is split into two partial flows, which flush around the pull wire carrier on different sides thereof. These two flushing flows can both respectively flow through a recess of the pull wire carrier. By the splitting of the flushing flow, both the exterior and the through-bore of the pull wire carrier can be cleaned particularly efficiently. By this flushing around and through, all flushing shadows inside the main body of the Albarran can be reached. This kind of thorough cleaning allows reconditioning of the instrument after the treatment. It is furthermore conceivable for the pull wire carrier to have further shapes in order to positively influence the flushing. Round shapes are to be preferred particularly in order to form a minimal flow resistance around the pull wire carrier.

Preferably, it is conceivable that a width of the pull wire carrier corresponds at most to two times the diameter of the through-bore. By this reduced width of the pull wire carrier, a particularly narrow and therefore easily flushable shape can be achieved. Furthermore, material and therefore costs can be saved by the reduction of the overall size.

One particularly advantageous exemplary embodiment provides that the pull wire carrier is made from a plastic, in particular from PEEK. In this case, PEEK has proven particularly suitable for withstanding the mechanical requirements. Furthermore, PEEK can be cleaned particularly thoroughly. The sliding resistance between the pull wire carrier and the metal shaft is also found to be sufficiently low when using PEEK.

An Albarran for achieving the aforementioned object has the features of claim 12. Accordingly, it is provided that the Albarran comprises a tubular shaft, at the distal end of which an Albarran lever is arranged and at the proximal end of which a main body having a drive body is arranged. The Albarran lever is in this case connected movably by means of at least one, preferably two, pull wires to a toggle on the drive body. The pull wires can be fixed at a proximal end in the drive body on a pull wire carrier. The pull wire carrier is configured as claimed in at least one of claims 1 to 11.

One particularly advantageous embodiment of the Albarran may provide that a flush connection is arranged on the drive body, the flush connection forming an acute angle with the shaft pointing in the distal direction of the Albarran. By this orientation of the flush connection, the flushing liquid is guided inside the drive body in the proximal direction of the Albarran. As soon as the flushing liquid flows through the flush connection, which may in particular be a Luer lock, into the interior of the drive body, it is split by the pull wire carrier into two partial flows before it leaves the drive body again, inter alia through the recess in the pull wire carrier. The arrangement of the flush connection inclined in the proximal direction can achieve the effect that the flushing liquid flows fully through the interior of the drive body, or of the main body. The residues dissolved by the flushing liquid, in particular the warm flushing liquid, leave the drive body in the distal direction or may be removed through one or two lateral outlets of the Albarran.

A further exemplary embodiment may provide that an axle of the Albarran lever is strengthened. This strengthening may involve the use of a particularly stable material and/or an increase in the axle diameter. By the formation of the friction clutch described above and the strengthening of the axle, a "breaking point" may thus be established, by which the risk of the patient being injured during the operation by a defective lever is minimized.

Figure 3:
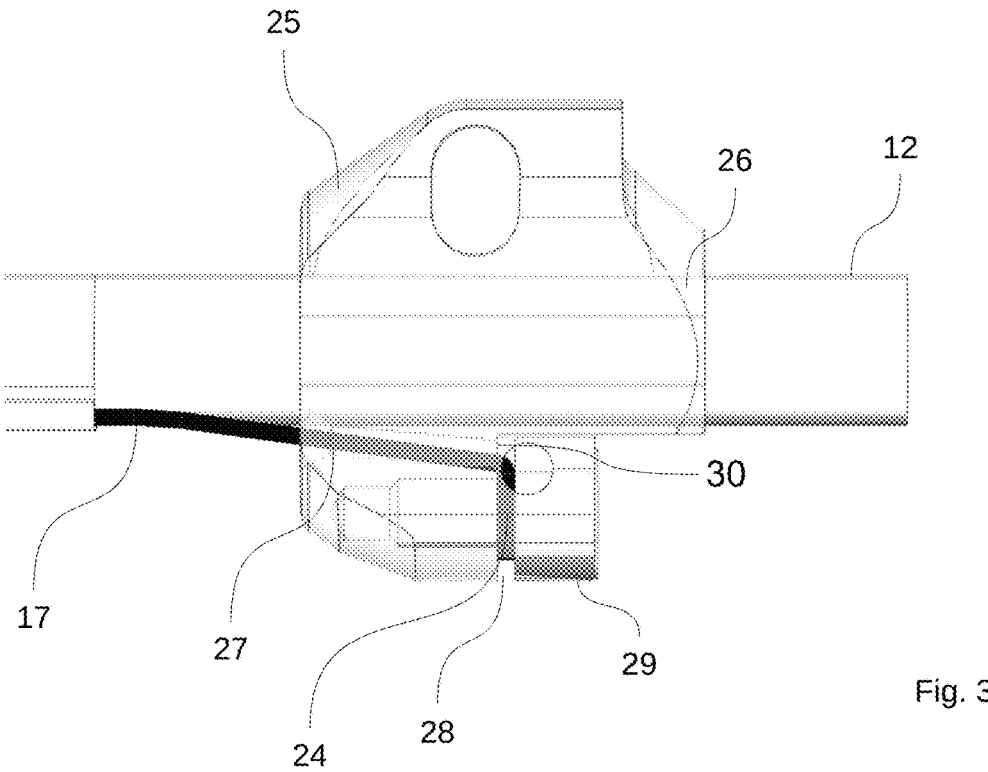
Figure 4:
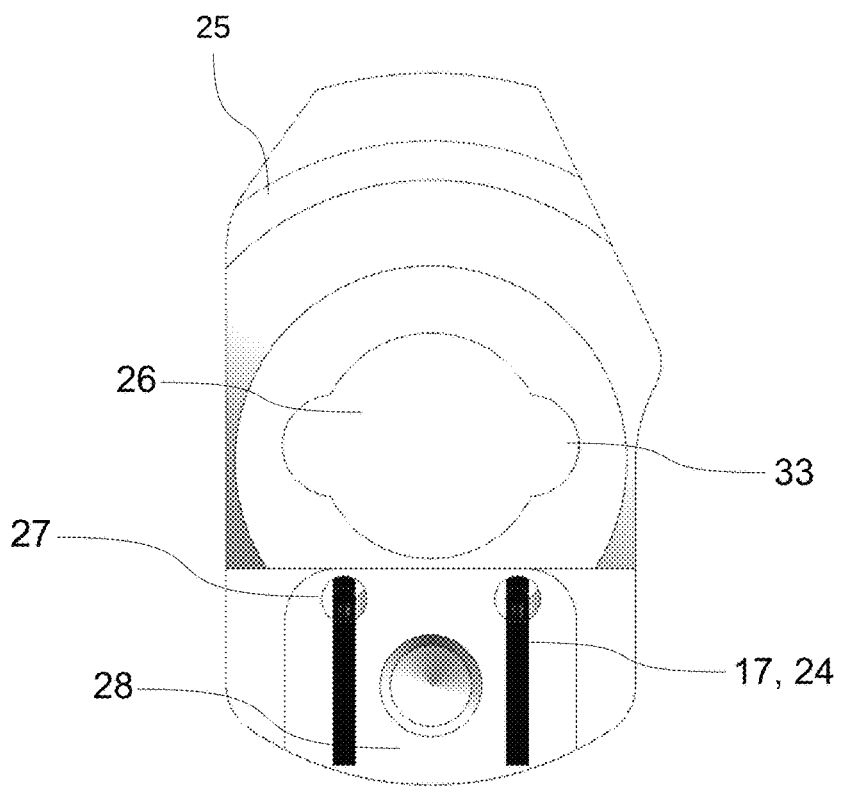
Figure 5:
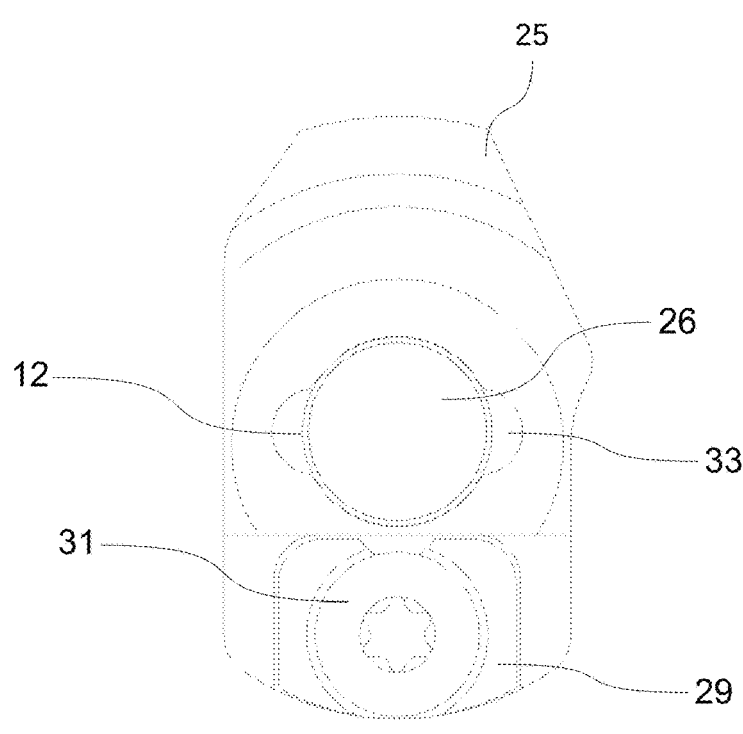
Figure 6:
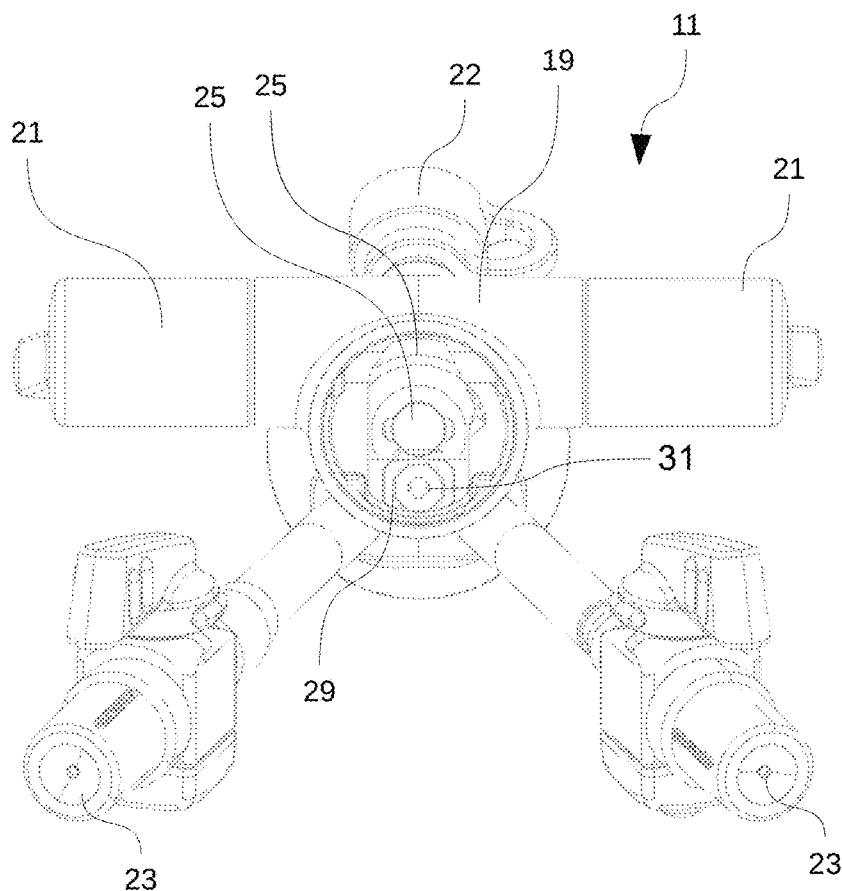
Figure 7:
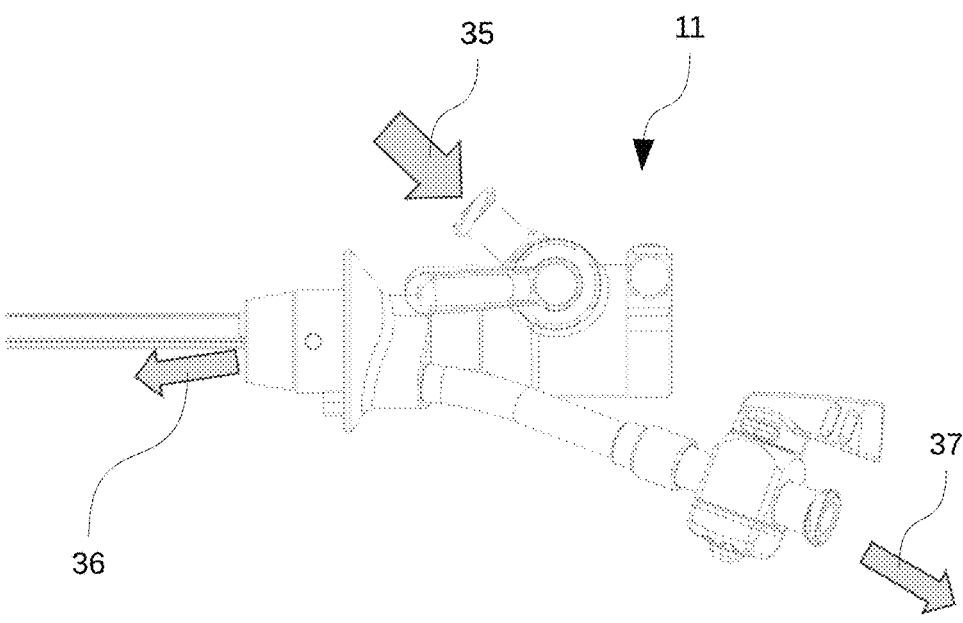
Figure 8:
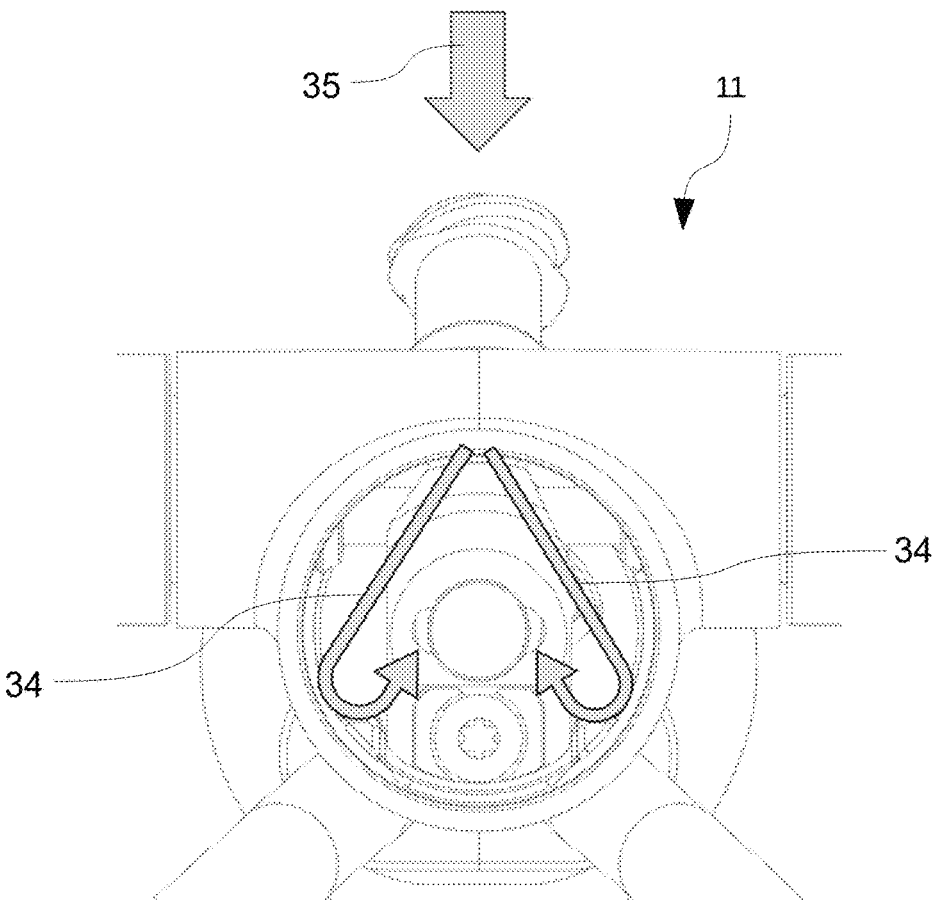

A preferred exemplary embodiment of the present invention will be explained in more detail below with the aid of the drawing, in which:

FIG. 1 shows a perspective view of an Albarran,
FIG. 2 shows a side view of a distal end of the Albarran according to FIG. 1,
FIG. 3 shows a side view of a pull wire carrier,
FIG. 4 shows a view of a proximal end of the pull wire carrier according to FIG. 3,
FIG. 5 shows a view of a proximal end of the pull wire carrier according to FIG. 3,
FIG. 6 shows a view of a proximal end of the Albarran according to FIG. 1, FIG. 7 shows a side view of a proximal end of the Albarran according to FIG. 1, and FIG. 8 shows a view of the proximal end of the Albarran according to FIG. 1.

FIG. 1 represents a possible exemplary embodiment of an Albarran 10. It should expressly be pointed out that the protective scope of the present patent application is not intended to be restricted to this exemplary embodiment. Rather, it is intended that further embodiments are also covered by the protective scope.

The Albarran 10 consists essentially of a main body 11 and a shaft 12 mounted on the main body 11. The shaft 12 is configured tubularly, and in order to treat persons it is guided with a distal end 13 forward into the body of the person. In this case, various medical or surgical instruments may be guided through the shaft 12. An Albarran lever, or a lever, 15 is arranged movably at the distal end 13 of the shaft 12 on an outer wall 14. This lever 15 is used by the operator during the treatment as an aid for carrying out further treatment steps. The lever 15 is in this case mounted pivotably about an axle 16 (FIG. 2). In order to move the lever 15, it can be actuated by means of pull wires 17. In the exemplary embodiment represented here, the lever 15 is assigned two pull wires 17. Nevertheless, embodiments in which the lever 15 has only one pull wire 17 are also conceivable. Exemplary embodiments in which the pull wire 17 is configured as a rod are furthermore conceivable.

The pull wires 17 extend parallel to the shaft 12 from the lever 15 to the proximal end 18 of the Albarran 10. In this case, the pull wires 17 are guided through the main body 11 and fastened in a drive body 19 of the main body 11. For actuation of the lever 15, the drive body 19 has a toggle 20 with two actuation means 21. By actuating, or rotating, these actuation means 21, the pull wires 17 are moved forward or back along the shaft 12 so that a pivoting movement of the lever 15 about the axle 16 is accomplished.

In order to be able to clean the Albarran 10, and in particular the main body 11, a flush connection 22 is arranged on the drive body 19. This flush connection 22 forms an acute angle with the shaft 12, and is therefore inclined in the direction of the distal end 13. A flushing liquid can be conveyed into the drive body 19 through this flush connection 22. The liquid may leave the main body 11 for example at a distal end again, or it may be discharged, or aspirated, through two outlets 23. While the flush connection 22 may be equipped with a cover in order to close the opening, the outlets 23 in the exemplary embodiment of the Albarran 10 as represented here respectively comprise a valve. The flushing liquid may be aspirated actively out from the main body 11 through the outlets 23 by a pump. In this way, the flushing through the main body 11, or of the entire Albarran 10, may be carried out in a particularly thorough way.

In order to be able to operate the lever 15 by means of the toggle 20, the proximal ends 24 of the pull wires 17 are fastened in the drive body 19 on a pull wire carrier 25. The pull wire carrier 25 comprises a through-bore 26, through which a tube, or the tubular shaft 12, is guided. In this case, the pull wire carrier 25 is mounted movably on the shaft 12. In order to receive the proximal ends 24 of the pull wires 17, the pull wire carrier 25 comprises two bores 27 below the through-bore 26. These bores 27 may be slightly inclined in relation to the through-bore 26. The proximal ends 24 of the pull wires 17 protrude in a receptacle 28 of the pull wire carrier 25 out of the latter. For sufficient retention of the pull wires 17, the proximal ends 24 are clamped in the receptacle 28 with a cover element 29. For this purpose, the proximal ends 24 are initially bent against a receptacle side 30 of the receptacle 28, so that the proximal ends 24 of the pull wires bear on the receptacle side 30 (FIG. 4). In the next step, the cover element 29 is fitted into the receptacle 28 and screwed with a screw 31 against the pull wire carrier 25. For this purpose, the cover element comprises a bore through which the screw 31 is guided. The pull wire carrier 25 in turn comprises a bore with a corresponding internal thread, in which the screw 31 can be screwed. In this case, the proximal ends 24 are clamped between an end side 32 of the cover element 29 and the receptacle side 30 of the pull wire carrier 25. By applying a predetermined torque to the screw 31, the proximal ends 24 of the pull wires 17 can be fixed in a very defined way.

This defined fixing is particularly advantageous since it may be used as a friction clutch during the use of the Albarran 10, in particular of the lever 15. There is a risk that, in the event of a malfunction or a defect, such a large force may be transmitted onto the lever 15 by means of the pull wires 17 that it breaks or causes different mechanical damage. The treatment is complicated as a consequence and may lead to avoidable traumatization of the patient. By the application of a predefined torque and by the nature of the fastening of the proximal ends 24 of the pull wires 17, the pull wires 17 slip through between the receptacle side 30 and the end side 12 before an excessive force can be applied. Damage to the lever 15 or another serious mechanical defect of the Albarran 10 is thereby avoided. Furthermore, the invention provides that the axle 16 of the lever 15 is strengthened or made from a particularly stable material, in order to withstand higher mechanical forces.

The above-described way in which the proximal ends 24 of the pull wires 17 are to be fastened to the pull wire carrier 25 is fundamentally advantageous since the fastening from the open proximal side of the main body 11 may be carried out purely mechanically. This proves to be performable particularly simply and freely from errors, Retensioning or repeated fixing of the pull wires 17 is also found to be particularly advantageous in this embodiment.

One particular challenge consists in reconditioning of the Albarran 10, or of the main body 11. In this case, it is particularly challenging to reach narrow intermediate spaces and dead volumes reliably with the flushing liquid. The invention provides that the through-bore 26 of the pull wire carrier 25 comprises at least one, two or more recesses 33 (FIG. 5). These recesses 33 are positioned parallel to the longitudinal axis of the through-bore 26 on the inner wall of the pull wire carrier 25, and substantially increase the area of the inner wall. Through the recesses 33, additional flushing liquid can pass through the pull wire carrier 25, specifically into the annular space between the shaft 12 and the through-bore 26. Even regions that have hitherto been difficult to access may therefore be reached by the flushing liquid, in particular a warm flushing liquid. Overall, the entire flushing behavior of the main body 11 can be improved by the recesses 33.

For particularly efficient input of the flushing liquid, the flush connection 22 is arranged directly over the pull wire carrier 25 (FIG. 6). The two outlets 23, with which the contaminated flushing liquid can be discharged rapidly and efficiently, are located on obliquely opposite sides of the flush connection 22. So that the flushing liquid is distributed particularly well inside the body 19, the pull wire carrier 25 is configured at an upper end in the manner of a wedge or trapezoid. In FIG. 8, the arrows 34 illustrate the way in which the flushing liquid is fed according to the arrow 35 through the flush connection into the drive body 19 and, because of the shape of the pull wire carrier 25, is flushed around the latter. Because of the oblique setting of the flush connection 22, the flushing liquid is initially sent in the proximal direction, where it is then guided into the recesses 33 and flushes around the space inside the pull wire carrier 25 as well as outside the pull wire carrier. As represented in FIG. 7, the flushing liquid may leave the main body 11 both in the distal direction 36 and through the outlets 23 in the proximal direction 37. It is conceivable for the flushing liquid to be fed through the flush connection 22 into the main body 11 under an elevated or variable or pulsed pressure. In particular because of the reduced shape of the pull wire carrier 25, particularly efficient and comprehensive flushing around and through the pull wire carrier 25 and the drive body 19 can take place.

LIST OF REFERENCES

10 Albarran
11 main body
12 shaft
13 distal end
14 outer wall
15 lever
16 axle
17 pull wire
18 proximal end
19 drive body
20 toggle
21 actuation means
22 flush connection
23 outlet
24 proximal end
25 pull wire carrier
26 through-bore
27 bore
28 receptacle
29 cover element
30 receptacle side
31 screw
32 end side
33 recess
34 arrow
35 arrow
36 distal direction
37 proximal direction

The invention claimed is:

1. A pull wire carrier for an Albarran, the pull wire carrier comprising a through-bore and a cover element, the pull wire carrier being configured to be mountable in a drive body of the Albarran and holding at least one pull wire configured for actuation of a lever of the Albarran, the pull wire carrier further comprising a receptacle into which the cover element is configured to be placed, the cover element being releasably connectable to the pull wire carrier and the at least one pull wire, the at least one pull wire being fixable between the cover element and a receptacle side of the receptacle of the pull wire carrier, wherein the cover element is inserted into the receptacle in a direction parallel to a longitudinal direction of the receptacle and parallel to at least a portion of the at least one pull wire, wherein the cover element is arranged in the receptacle with a predetermined pressure, wherein the cover element is configured to be screwed with a defined torque against the receptacle side of the receptacle of the pull wire carrier, and wherein a proximal end of the at least one pull wire is configured to be disposed against the receptacle side of the receptacle of the pull wire carrier and can be clamped between the receptacle side of the receptacle of the pull wire carrier and the cover element, so that a friction clutch of the pull wire is formed between the receptacle side and the cover element.

2. The pull wire carrier as claimed in claim 1, wherein the cover element is configured to be clamped, pressed, adhesively bonded, and/or screwed in the receptacle of the pull wire carrier.

3. The pull wire carrier as claimed in claim 1, wherein the through-bore is one of two through-bores for accommodating the at least one pull wire arranged in the pull wire carrier, the two through-bores extending from a distal side of the pull wire carrier to a receptacle side of the receptacle of the pull wire carrier.

4. A pull wire carrier for an Albarran having a through-bore, this pull wire carrier being mounted in a drive body of the Albarran and at least one pull wire for actuation of a lever of the Albarran being braceable on the pull wire carrier, as claimed in claim 1, wherein the through-bore, which is circular, comprises one or more recesses for receiving a tube on an inner wall, which extend parallel to a longitudinal axis, over an entire length of the through-bore.

5. The pull wire carrier as claimed in claim 4, wherein the one or more recesses occupy from 10% to 40% of a cross-sectional area of the inner wall.

6. The pull wire carrier as claimed in claim 1, wherein a diameter of the through-bore is greater than a diameter of a tube that can be received in the through-bore, an annular gap being formed between an inner wall of the through-bore and the tube.

7. The pull wire carrier as claimed in claim 1, wherein a cross section of the pull wire carrier has a shape of a wedge or trapezoid, the cross section tapering toward an upper end of the pull wire carrier.

8. The pull wire carrier as claimed in claim 1, wherein a width of the pull wire carrier equals at most to two times a diameter of the through-bore.

9. The pull wire carrier as claimed in claim 1, wherein the pull wire carrier is formed from a plastic.

10. An Albarran having a tubular shaft, at a distal end of which an Albarran lever is arranged and at a proximal end of which a main body having a drive body is arranged, the Albarran lever being movable by at least one pull wire by a toggle on the drive body and a proximal end of the at least one pull wire being fixable in the drive body on a pull wire carrier as claimed in claim 1.

11. The Albarran as claimed in claim 10, wherein a flushing connection is arranged on the drive body, the flushing connection forming an acute angle with the shaft pointing in a distal direction of the Albarran.

12. The Albarran as claimed in claim 11, wherein the flushing connection is arranged directly above the pull wire carrier on the drive body, the pull wire carrier has a shape of a wedge or a trapezoid, and a flushing liquid flow that impinges on the pull wire carrier can be divided into two partial flows.

* * * * *